US00PP25567P2

(12) United States Plant Patent
Oprins

(10) Patent No.: US PP25,567 P2
(45) Date of Patent: May 19, 2015

(54) ***HYDRANGEA* PLANT NAMED 'HAOP012'**

(50) Latin Name: *Hydrangea aspera*
Varietal Denomination: Haop012

(71) Applicant: Jan Oprins, Rijkevorsel (BE)

(72) Inventor: Jan Oprins, Rijkevorsel (BE)

(73) Assignee: Oprins Plant N.V., Rijkevorsel (BE)

( * ) Notice: Subject to any disclaimer, the term of this patent is extended or adjusted under 35 U.S.C. 154(b) by 86 days.

(21) Appl. No.: 13/987,872

(22) Filed: Sep. 11, 2013

(51) Int. Cl.
*A01H 5/00* (2006.01)

(52) U.S. Cl.
USPC ..... Plt./250

(58) Field of Classification Search
CPC ..... A01H 5/02; A01H 5/00
USPC ..... Plt./250
See application file for complete search history.

*Primary Examiner* — Kent L Bell
(74) *Attorney, Agent, or Firm* — Penny J. Aguirre

(57) ABSTRACT

A new cultivar of *Hydrangea aspera* named 'Haop012' that is characterized by its leaves that are chocolate brown-red on the lower surface of mature leaves, its translucent pink sterile flowers, and its purple-blue fertile flowers with purple-blue anthers.

2 Drawing Sheets

Botanical classification: *Hydrangea aspera.*
Varietal denomination: 'Haop012'.

BACKGROUND OF THE INVENTION

The present invention relates to a new and distinct cultivar of *Hydrangea aspera* and will be referred to hereafter by its cultivar name, 'Haop012'. 'Haop012' represents a new lacecap type *Hydrangea*, a deciduous shrub grown for landscape use and for use as a potted plant.

The new cultivar of *Hydrangea* arose from a breeding program conducted by the Inventor in Rijkevorsel, Belgium. 'Hoap012' originated as a seedling that arose from seed planted from open pollination of 'Koki' (not patented) in 2010. 'Hoap012' was selected as a single unique plant in June of 2010 from amongst the resulting seedlings.

Asexual propagation of the new cultivar was first accomplished by the Inventor by softwood cuttings in Rijkevorsel, Belgium in June 2010. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Haop012' as a unique cultivar of *Hydrangea.*

1. 'Haop012' exhibits leaves that are distinctively chocolate brown-red on the lower surface.
2. 'Haop012' exhibits clear pink sterile flowers.
3. 'Haop012' exhibits purple-blue fertile flowers with purple-blue anthers.

'Koki', the female parent of 'Haop012', differs from 'Haop012' in having less conspicuous sterile flowers that are beige to dull pink in color, a less vigorous growth rate, and in being shorter in height. 'Haop012' can be most closely compared to the cultivars 'Kawakami' (not patented) and 'Mauvette' (not patented). 'Kawakami' is similar to 'Haop012' in having purple-blue colored fertile flowers. 'Kawakami' differs from 'Haop012' in having gray-green leaves on both leaf surfaces and off-white to whitish-pink sterile flowers. 'Mauvette' differs from 'Haop012' in having smaller, narrower, dark green leaves and lilac colored sterile flowers.

BRIEF DESCRIPTION OF THE DRAWINGS

The accompanying colored photographs illustrate the overall appearance and distinct characteristics of the new *Hydrangea*, 'Haop012', as grown outdoors in Rijkevorsel, Belgium. The photographs were taken of a two year-old plant of 'Haop012' as grown in a 23-cm container.

The photograph in FIG. 1 provides a side view of a plant of 'Haop012'.

Figure 1:
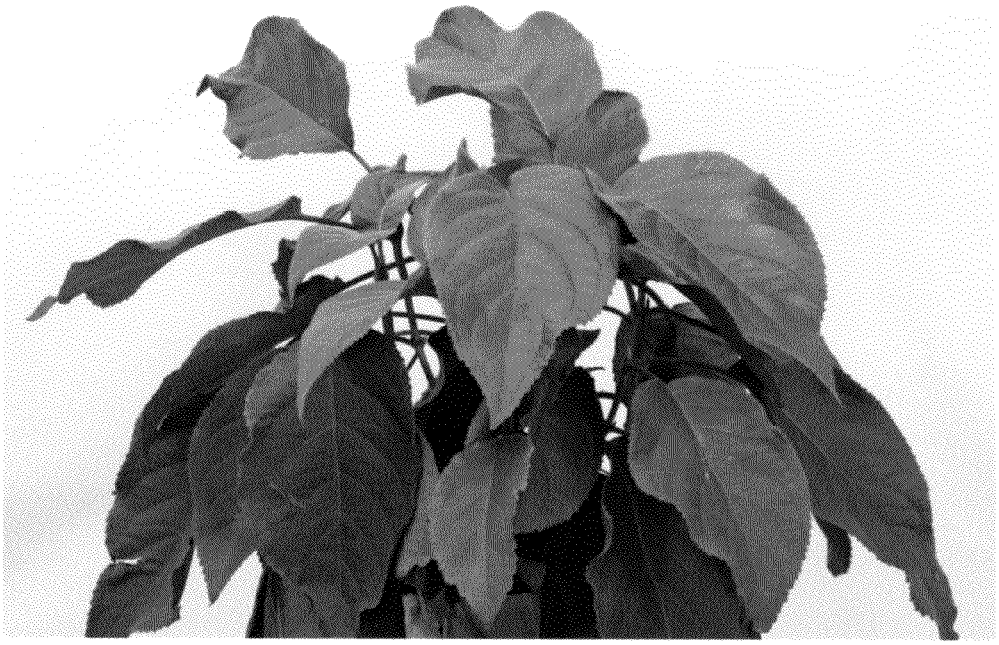
Figure 2:
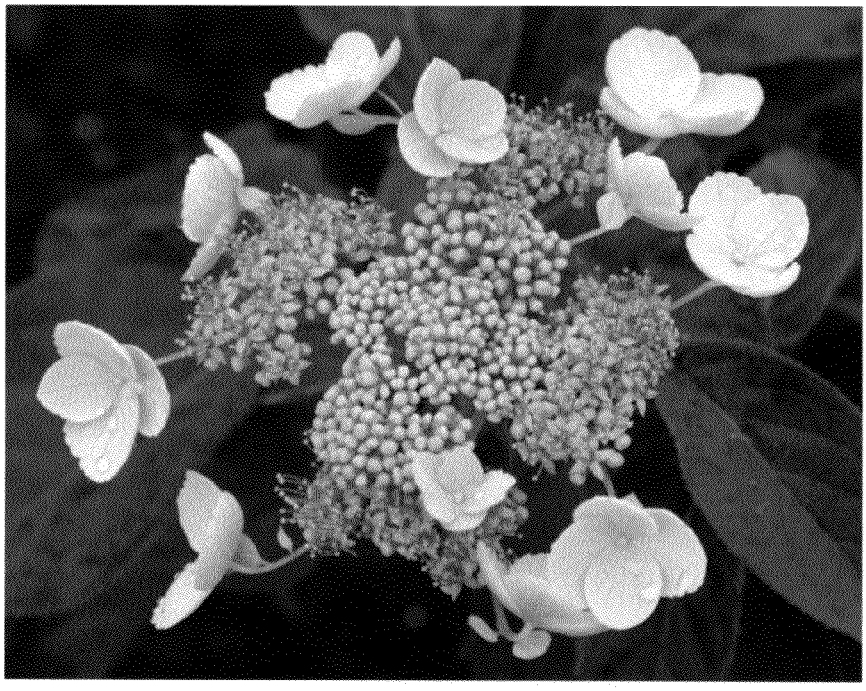

The photograph in FIG. 2 provides a close-up view of an inflorescence of 'Haop012'.

Figure 3:
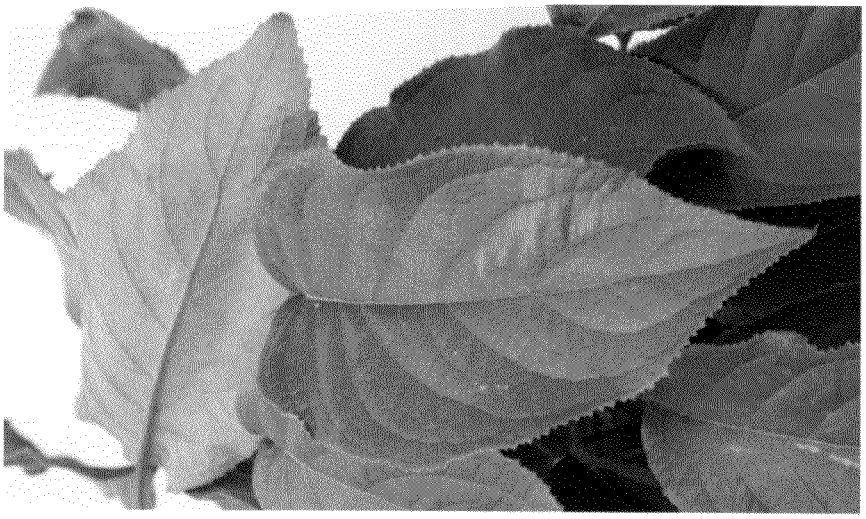

The photograph in FIG. 3 provides a close-up view of the foliage of 'Haop012'.

The colors in the photographs may differ slightly from the color values cited in the detailed botanical description, which accurately describe the colors of the new *Hydrangea.*

BOTANICAL DESCRIPTION OF THE PLANT

The following is a detailed description of two year-old plants of 'Haop012' as grown outdoors in 23-cm containers in Stroe, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Approximately three weeks in June and July in The Netherlands.

*Plant type.*—Deciduous shrub, lacecap type *Hydrangea.*

*Plant habit.*—Compact mound.

*Height and spread.*—Reaches about 27.9 cm in height and 43.8 cm in spread.

*Hardiness.*—U.S.D.A. zone 7.

*Diseases resistance.*—No particular susceptibility or resistance to diseases has been observed.

*Root description.*—Fine.

*Propagation.*—Softwood stem cuttings.

*Growth rate and vigor.*—Moderately vigorous.

Stem description:

*Stem shape.*—Round, solid.

*Stem strength.*—Strong.

*Stem color.*—New growth; 183C, mature growth; ranging between 199A to N199B and N199C.

*Stem size.*—Average of 14.1 cm in length, average of 5 mm in diameter.

*Stem surface.*—Slightly glossy, moderately to densely covered with strigose hairs, average length of 1.5 mm and 199D in color.

*Internode length.*—Average of 5 cm.

*Branching.*—Average of 10 lateral branches.

Foliage description:

*Leaf shape.*—Ovate.

*Leaf arrangement.*—Opposite.

*Leaf division.*—Simple.

*Leaf base.*—Obtuse.

*Leaf apex.*—Acuminate to acute.

*Leaf margins.*—Irregularly serrate.

*Leaf venation.*—Pinnate, upper surface 178A and lower surface 185A in color.

*Leaf size.*—Matures to an average of 16 cm in length and 8.6 cm in width.

*Leaf attachment.*—Petiolate.

*Leaf surface.*—Upper surface; slightly glossy and slightly rugose, lower surface; dull and moderately rugose, both surfaces densely covered with short strigose hairs 156D in color, an average of 0.5 mm in length on the upper surface and 0.3 mm on the lower surface.

*Leaf color.*—Young foliage upper surface; N137B, young foliage lower surface; a blend of 176B and 182B, mature foliage upper surface; a blend of N137A and 147A, mature foliage lower surface; a blend of 176B and 182B.

*Petioles.*—An average of 6 cm in length and 3 mm in diameter, upper surface a blend of 187A and 200C and lower surface a blend of 185A and 187C in color, both upper and lower surfaces dull and covered with short strigose hairs an average of 0.3 mm in length and 156D in color.

Inflorescence description:

*Inflorescence type.*—Terminal panicle, lacecap in form comprised of a center region of fertile flowers surrounded by an outer ring of single sterile flowers.

*Lastingness of inflorescence.*—Persistent but color is retained for about 3 weeks.

*Inflorescence number.*—One per lateral or sublateral stem if pinched.

*Inflorescence size.*—Average of 5.6 cm in height and 10.2 cm in diameter.

*Flower number.*—Average of 10 sterile flowers and 500 fertile flowers per panicle.

*Flower fragrance.*—None.

*Flower aspect.*—Upright.

*Flower size.*—Sterile flowers; an average of 3 cm in diameter and 6 mm in depth, fertile flowers; an average of 7 mm in diameter and depth.

*Flower type.*—Rotate.

*Flower buds.*—Sterile flowers; average of 8 mm in length and 7 mm in diameter prior to opening, broad ovate in shape, 37B in color fading to 38A towards the top, fertile flowers; average of 3 mm in width and 2 mm in diameter, obovate in shape, 85D in color.

*Peduncles.*—Moderately strong, average of 3 cm in length and 3 mm in width, average angle of 10° from vertical, 39D in color.

*Pedicels.*—Sterile flowers; held at an average angle of 65° from vertical, an average of 2.1 cm in length and 1 mm in diameter, moderately weak strength, 50C in color, surface dull and moderately covered with very short soft hairs an average length of 0.05 mm and NN155B in color, fertile flowers; held at an average angle of 45° from vertical, an average of 2 mm in length and 1 mm in diameter, moderately weak in strength, 39D in color, surface is dull and moderately covered with very short soft hairs an average length of 0.03 mm and NN155B in color.

*Petals.*—Fertile flowers; average of 5, rotate in arrangement, ovate in shape, entire margin, acute apex, cuneate base, average of 2.5 mm in length and 1 mm in width, upper surface glabrous and dull, lower surface glabrous and slightly glossy, color of upper surface when opening and when fully opened 76A, lower surface when opening and when fully opened 76A with 86D at the tip, color not fading, sterile flowers; an average of 4, rotate arrangement but typically not opening with fused apex, base, and margins, open petals; acute apex, cuneate base, entire margins, ovate in shape, an average of 1 mm in length and width, upper surface not visible in closed flowers, lower surface; glabrous, dull, and 76C to 76D in color.

*Sepals.*—Sterile flowers; average of 4, rotate arrangement, orbicular to broadly ovate in shape, an average of 1.5 cm in length and width, obtuse to retuse apex, broadly cuneate base, upper surface glabrous and very lightly glossy, lower surface glabrous and dull, denticulate to crenulate margins, color when opening upper and lower surfaces; 38C to 38D, color when fully opened upper surface; 56C with veins 51D fading to 56C and color when fully opened on lower surface; 51D fading to 56C, fertile flowers; 5, rotate in arrangement, triangular in shape, entire margin, broad acuminate apex, broad cuneate base, average of 0.5 mm in length and 0.75 mm in width, both surfaces are glabrous and dull, color of upper and lower surface on opening and open flower 150D, color is not fading.

Reproductive organs: (fertile flowers).

*Stamens.*—Average of 10, anther is short oblong in shape, 0.75 mm in length and N187D in color, filament is 5 mm in length, pollen is moderate in quantity and 156D in color.

*Pistils.*—Average of 2, an average of 1.5 mm in length, stigma is clavate shaped and 85C to 85D in color, style is an average of 0.75 mm in length and 85C in color, ovary is 150D in color.

*Fruit and seed.*—Has not been observed.

It is claimed:

1. A new and distinct cultivar of *Hydrangea* plant named 'Haop012' substantially as herein illustrated and described.

* * * * *